United States Patent
Wang et al.

(10) Patent No.: US 9,838,612 B2
(45) Date of Patent: Dec. 5, 2017

(54) INSPECTING DEVICE AND METHOD FOR INSPECTING INSPECTION TARGET

(71) Applicant: Test Research, Inc., Taipei (TW)

(72) Inventors: Yeong-Feng Wang, Taipei (TW); Kuang-Pu Wen, Hsinchu County (TW)

(73) Assignee: Test Research, Inc., Taipei (TW)

( * ) Notice: Subject to any disclaimer, the term of this patent is extended or adjusted under 35 U.S.C. 154(b) by 275 days.

(21) Appl. No.: 14/797,188

(22) Filed: Jul. 13, 2015

(65) Prior Publication Data
US 2017/0019578 A1    Jan. 19, 2017

(51) Int. Cl.
| | |
|---|---|
| *H04N 7/18* | (2006.01) |
| *H04N 5/235* | (2006.01) |
| *G01N 21/88* | (2006.01) |
| *H04N 5/225* | (2006.01) |
| *G06T 7/00* | (2017.01) |

(52) U.S. Cl.
CPC ....... *H04N 5/2354* (2013.01); *G01N 21/8806* (2013.01); *G06T 7/0004* (2013.01); *H04N 5/2256* (2013.01); *G01N 2021/8845* (2013.01); *G01N 2201/061* (2013.01); *G06T 2207/30141* (2013.01)

(58) Field of Classification Search
CPC ............ G01B 11/00; G06K 9/52; G06K 9/00
USPC ...................... 348/86–95, 125–126
See application file for complete search history.

(56) References Cited

U.S. PATENT DOCUMENTS

| | | |
|---|---|---|
| 7,356,176 B2 | 4/2008 | Fujii et al. |
| 7,394,084 B2 | 7/2008 | Kuriyama et al. |
| 2012/0033066 A1* | 2/2012 | Wieser ............... G01B 11/0608 348/87 |

FOREIGN PATENT DOCUMENTS

| | | |
|---|---|---|
| CN | 100433962 C | 11/2008 |
| JP | 2007-64801 A | 3/2007 |
| TW | 1345053 B | 7/2011 |
| TW | 201415047 A | 4/2014 |
| TW | 1442044 B | 6/2014 |

* cited by examiner

*Primary Examiner* — Andy Rao
(74) *Attorney, Agent, or Firm* — CKC & Partners Co., Ltd.

(57) ABSTRACT

An inspecting device for inspecting an inspection target is provided. The inspecting device includes a mono-color image-retrieving module, illuminating modules and a control module. The mono-color image-retrieving module is disposed above the inspection target with an optical axis orienting toward the inspection target. Each of the illuminating modules includes light-emitting elements of different colors. The control module controls the illuminating modules to sequentially generate illuminating lights both in an order of different colors and different incident angles to further control the mono-color image-retrieving module to sequentially retrieve mono-color images each in response to one illumination of the illuminating lights. The control module performs an inspection of the inspection target based on the mono-color images.

16 Claims, 5 Drawing Sheets

INSPECTING DEVICE AND METHOD FOR INSPECTING INSPECTION TARGET

BACKGROUND

Field of Disclosure

The present disclosure relates to an inspecting technology. More particularly, the present disclosure relates to an inspecting device and a method for inspecting an inspection target.

Description of Related Art

Either during or after a production process of an electronic device, it is important to perform inspection to determine the condition of the mounted electronic components and/or the soldered parts formed on the electronic device. Image processing is widely used in conventional inspecting technology, in which the image to be processed is obtained by using light sources that illuminates the object to be inspected and a camera for retrieving the image.

In such a system, a multi-color image-retrieving module is used to retrieve images. However, color filter on the image-retrieving module reduces resolution. Also different incident angles of different color lights may result in different reflection rate due to the different materials and coating on the device. Further, some colors are not easy to be distinguished from each other. The accuracy, resolution and color saturation of the inspection may thus be affected due to the foregoing reasons.

Accordingly, what is needed is an inspecting device and a method for inspecting an inspection target to address the issues mentioned above.

SUMMARY

An aspect of the present disclosure is to provide an inspecting device for inspecting an inspection target. The inspecting device includes a mono-color image-retrieving module, a plurality of illuminating modules and a control module. The mono-color image-retrieving module is disposed above the inspection target with an optical axis orienting toward the inspection target. Each of the illuminating modules includes a plurality of light-emitting elements of different colors around the optical axis such that an illumination angle between the optical axis and each of the illuminating modules is within a specified angular range with respect to one of a plurality target areas on the inspection target. The control module is electrically connected to the illuminating modules and the mono-color image-retrieving module to control the illuminating modules to sequentially generate a plurality of illuminating lights both in an order of different colors and different incident angles to further control the mono-color image-retrieving module to sequentially retrieve a plurality of mono-color images each in response to one illumination of the illuminating lights. The control module performs an inspection of the inspection target based on the mono-color images.

Another aspect of the present disclosure is to provide an inspecting method for inspecting an inspection target used in an inspecting device. The inspecting method includes the steps outlined below. A mono-color image-retrieving module is disposed above the inspection target with an optical axis orienting toward the inspection target. A plurality of illuminating modules are controlled to sequentially generate a plurality of illuminating lights both in an order of different colors and different incident angles, wherein each of the illuminating modules comprises a plurality of light-emitting elements of different colors around the optical axis such that an illumination angle between the optical axis and each of the illuminating modules is within a specified angular range with respect to one of a plurality target areas on the inspection target. The mono-color image-retrieving module is controlled to sequentially retrieve a plurality of mono-color images each in response to one illumination of the illuminating lights. An inspection of the inspection target is performed based on the mono-color images.

These and other features, aspects, and advantages of the present disclosure will become better understood with reference to the following description and appended claims.

It is to be understood that both the foregoing general description and the following detailed description are by examples, and are intended to provide further explanation of the disclosure as claimed.

BRIEF DESCRIPTION OF THE DRAWINGS

The disclosure can be more fully understood by reading the following detailed description of the embodiment, with reference made to the accompanying drawings as follows.

DETAILED DESCRIPTION

Figure 1:
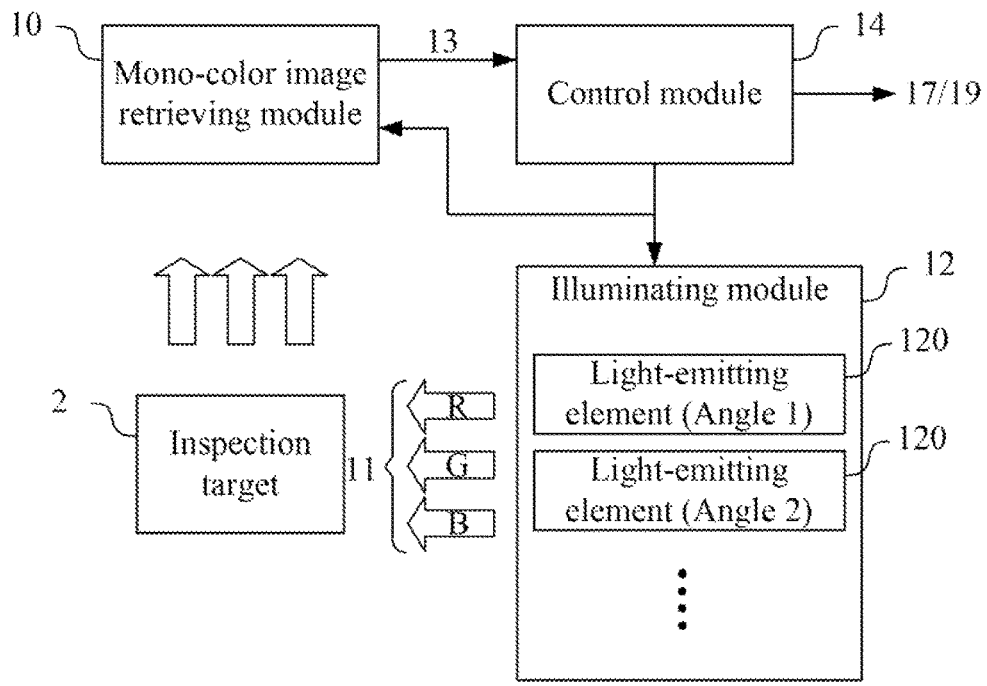
FIG. 1 is a block diagram of a an inspecting device in an embodiment of the present disclosure.

Reference will now be made in detail to the present embodiments of the disclosure, examples of which are illustrated in the accompanying drawings. Wherever possible, the same reference numbers are used in the drawings and the description to refer to the same or like parts.

Figure 2:
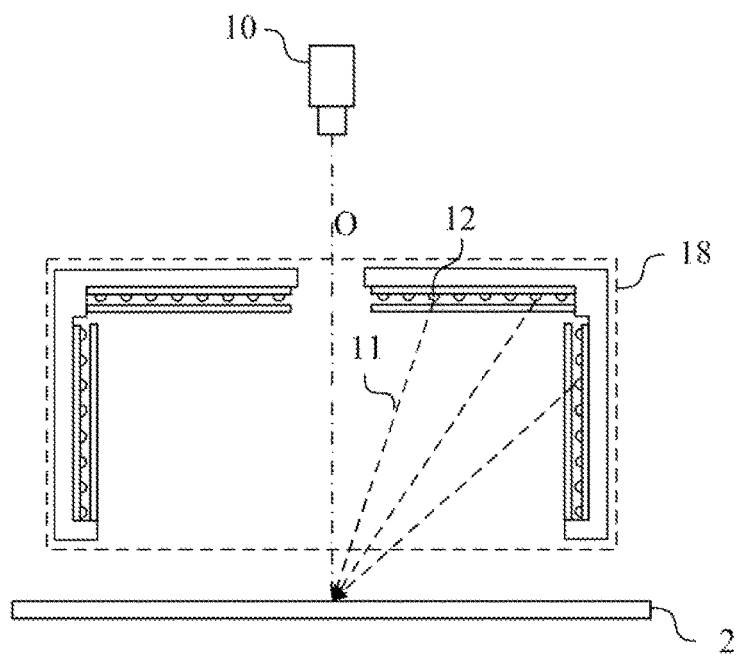
FIG. 2 is a diagram of the mono-color image-retrieving module, a plurality of illuminating modules and an inspection target in an embodiment of the present disclosure.

Reference is made to FIG. 1 and FIG. 2 at the same time. FIG. 1 is a block diagram of an inspecting device 1 in an embodiment of the present disclosure. The inspecting device 1 includes a mono-color image-retrieving module 10, an exemplarily illustrated illuminating module 12 and a control module 14.

FIG. 2 is a diagram of the mono-color image-retrieving module 10, a plurality of illuminating modules 12 and an inspection target 2 in an embodiment of the present disclosure. The inspecting device 1 is used to perform inspection on the inspection target 2. In different embodiments, the inspection target 2 can be any kind of electronic devices, e.g. a substrate including a circuit formed thereon.

The mono-color image-retrieving module 10 is disposed above the inspection target 2 with an optical axis O orienting toward the inspection target 2. The mono-color image-retrieving module 10 is able to retrieve mono-color images that contain grayscale information only.

A plurality of illuminating modules 12 are included in the inspecting device 1, as shown in FIG. 2, in which only one of the illuminating modules 12 is exemplarily illustrated in FIG. 1. The illuminating modules 12 can be integrated in an illuminator 18 illustrated in FIG. 2. In different embodiments, the illuminating modules 12 can be disposed above the inspection target 2 by using any possible configuration.

Each of the illuminating modules 12 includes a plurality of light-emitting elements 120 to generate illuminating lights 11 of different colors, such as a red color light (labeled as R in FIG. 1), a green color light (labeled as G in FIG. 1) and a blue color light (labeled as B in FIG. 1).

Each of the illuminating modules 12 is around the optical axis O such that an illumination angle between the optical axis O and each of the illuminating modules 12 is within a specified angular range with respect to one of a plurality target areas on the inspection target 2, such as the angular ranges Angle 1, Angle 2, . . . labeled in FIG. 1. It is appreciated that the number of the light-emitting elements 120 and the number of the angle ranges can be different in various embodiments and are not limited thereto.

The control module 14 is electrically connected to the illuminating modules 12. In an embodiment, the control module 14 controls the illuminating modules 12 to sequentially generate a plurality of illuminating lights 11 in an order of different colors. For example, the control module 14 controls the illuminating modules 12 to sequentially generate red color lights in a first time period, generate the green color lights in a subsequent second time period and generate the blue color lights in a subsequent third time period to the inspection target 2. It is appreciated that the order of the colors can be different in various embodiments and is not limited thereto.

In another embodiment, the control module 14 controls the illuminating modules 12 to sequentially generate a plurality of illuminating lights 11 in an order of different illuminating angles. For example, the control module 14 controls the illuminating modules 12 to generate the red color lights from a first and a second illuminating angles in a first time period, generate both of the green color lights and the blue color lights from a third illuminating angle in a subsequent second time period and generate the blue color lights from a fourth and a fifth illuminating angles in a subsequent third time period to the inspection target 2. It is appreciated that the order of the illuminating angles and the colors of the light corresponding to each of the illuminating angles can be different in various embodiments and is not limited thereto.

The control module 14 is electrically connected to mono-color image-retrieving module 10. The control module 14 further controls the mono-color image-retrieving module 10 to sequentially retrieve a plurality of mono-color images 13 each in response to one illumination of the illuminating lights 11. It is appreciated that the control module 14 controls the mono-color image-retrieving module 10 to retrieve the mono-color images 13 synchronously with the illumination of the corresponding illuminating lights 11.

The control module 14 performs an inspection of the inspection target 2 based on the mono-color images 13.

In an embodiment, the control module 14 performs the inspection by obtaining a profile 17 of the inspection target 2 according to the mono-color images 13 retrieved based on the illuminating lights 11 in the order of the different illumination angles. In an embodiment, the profile is obtained by performing trigonometric measurements based on information of the mono-color images 13. In an embodiment, the profile is identical to contour lines of the components in the inspection target 2.

In an embodiment, the control module 14 performs the inspection by obtaining a multi-color image 19 by adding corresponding colors to the mono-color images 13 retrieved based on the illuminating lights 11 in the order of the different colors covering all of the target areas and integrating the colored mono-color images into the multi-color image 19. For example, when a first, a second and a third mono-color images 13 are sequentially retrieved based on the red, blue and green color lights, the red, blue and green colors are correspondingly superimposed on the first, the second and the third mono-color images 13 to generate a red colored image, a blue colored image and a green colored image (not illustrated). Subsequently, the red colored image, a blue colored image and a green colored image are integrated into the multi-color image 19.

Figure 3:
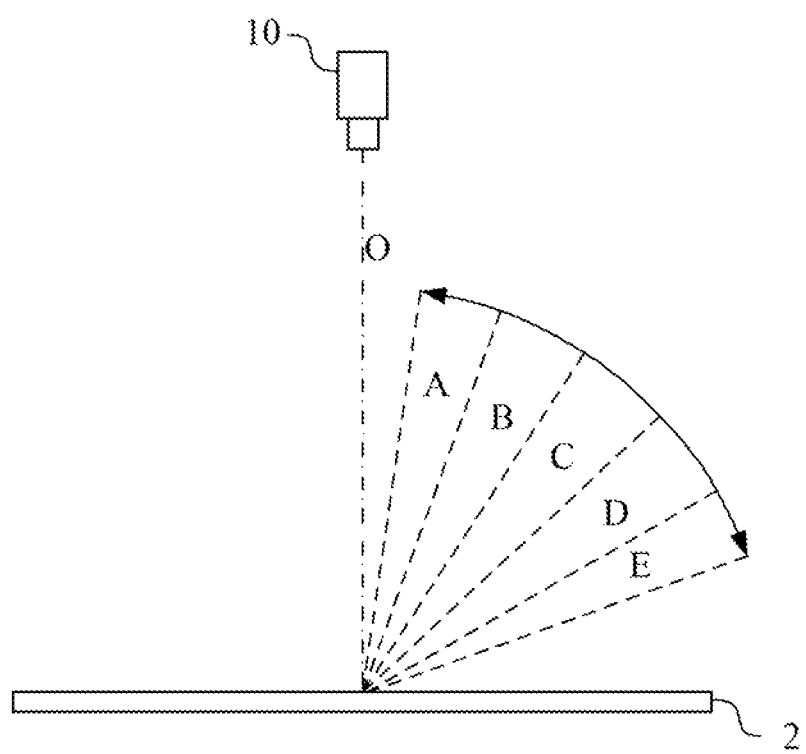
FIG. 3 is a diagram of the mono-color image-retrieving module, target areas and the inspection target in an embodiment of the present disclosure.

Reference is now made to FIG. 1 and FIG. 3 at the same time. FIG. 3 is a diagram of the mono-color image-retrieving module 10 target areas A-E and the inspection target 2 in an embodiment of the present disclosure.

According to the illuminating angles of the illuminating modules 2, there are five target areas A-E corresponding to different angular ranges.

In an embodiment, the control module 14 controls the illuminating modules 12 to sequentially generate the illuminating lights 11 with different colors each illuminating at least one part of the target areas. For example, the control module 14 controls the illuminating modules 12 to sequentially generate the red color lights to illuminate the target areas A and B, the green color lights to illuminate the target area C and the blue color lights to illuminate the target areas D and E. The control module 14 further controls the mono-color image-retrieving module 10 to sequentially retrieve the mono-color images 13 in response to the respective illuminating lights 11.

Under such a condition, the control module 14 can perform the inspection of the inspection target 2 based on different angles of illumination.

In an embodiment, the control module 14 controls the illuminating modules 12 to sequentially generate different colors of the illuminating lights 11 illuminating all the target areas A-E. For example, the control module 14 controls the illuminating modules 12 to sequentially generate the red color lights to illuminate the target areas A-E, the green color lights to illuminate the target areas A-E and the blue color lights to illuminate the target areas A-E. The control module 14 further controls the mono-color image-retrieving module 10 to sequentially retrieve the mono-color images 13 accordingly.

As mentioned earlier, the control module 14 can performs the inspection by obtaining a multi-color image 19 by adding corresponding colors to the mono-color images 13 retrieved based on the illuminating lights 11 in the order of the different colors covering all of the target areas and integrating the colored mono-color images into the multi-color image 19.

In conventional inspecting technology, a multi-color image-retrieving module is used to retrieve images in response to the illumination of different colors and different angles at the same time. At first, a color filter using such as but not limited to Bayer filter pattern is included such that different colors of lights are allowed to be transmitted in different pixels. However, it is difficult to distinguish between different colors when the wavelengths of lights of these colors are close.

Moreover, different incident angles of different color lights may result in different reflection rate due to the different materials and coating on the inspection target 2. For example, since the reflective rate of the copper in response to the blue color is not high, information of the section of the inspection target 2 formed by the copper may be lost due to such a reason, and the width of the components in the inspection target 2 in the obtained image may be different when different colors of light is used, which is undesirable.

By using the inspecting device 1 of the present disclosure, a greater resolution, a better color saturation and reasonable widths of the components in of the components in the image of the inspection target 2 can be obtained since the ambiguity between different colors can be avoided due to the absent of the color filter and the full illuminating angles. The profile of the inspection target 2 can be obtained more accurately, and the resolution of the multi-color image of the of the inspection target 2 can be greater.

It is appreciated that in different embodiments, the colors needed to be illuminated, the order of the colors to be illuminated, the number of the target areas and the intensity of the illumination of different colors can be different depending on the type of the inspection target 2 and are not limited thereto.

Figure 4:
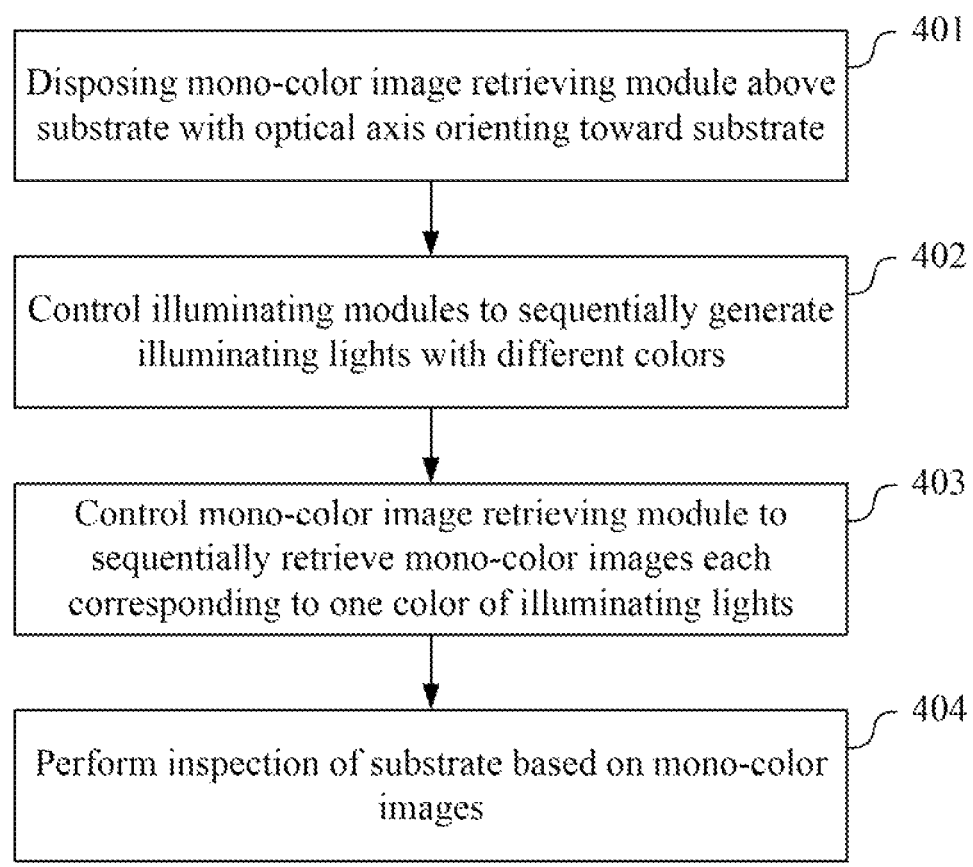
FIG. 4 is a flow chart of an inspecting method in an embodiment of the present disclosure.

FIG. 4 is a flow chart of an inspecting method 400 in an embodiment of the present disclosure. The inspecting method 400 can be used in the inspecting device 1 illustrated in FIG. 1. The inspecting method 400 includes the steps outlined below (The steps are not recited in the sequence in which the steps are performed. That is, unless the sequence of the steps is expressly indicated, the sequence of the steps is interchangeable, and all or part of the steps may be simultaneously, partially simultaneously, or sequentially performed).

In step 401, the mono-color image-retrieving module 10 is disposed above the inspection target with the optical axis O orienting toward the inspection target 2.

In step 402, the illuminating modules 12 are controlled to sequentially generate the illuminating lights 11 with different colors.

In step 403, the mono-color image-retrieving module 10 is controlled to sequentially retrieve the mono-color images 13 each in response to one color of the illuminating lights 11.

In step 404, an inspection of the inspection target 2 is performed based on the mono-color images 13.

Figure 5:
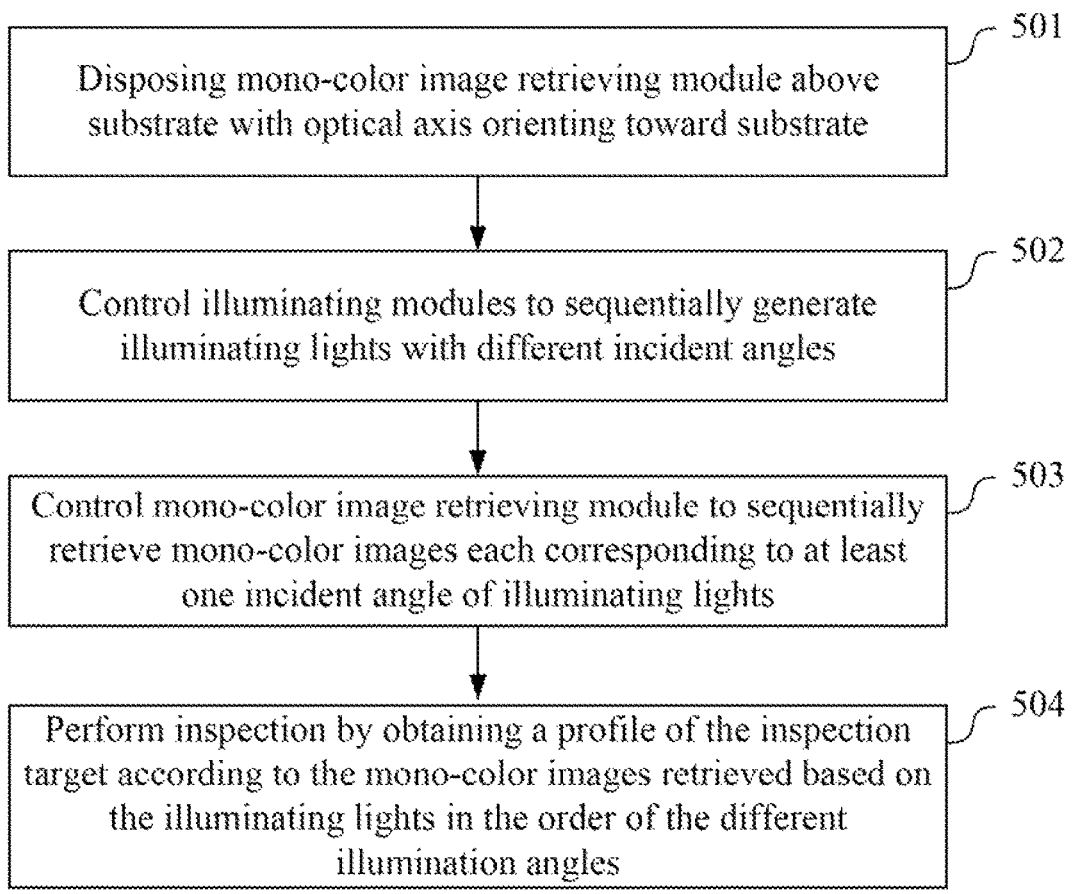
FIG. 5 is a detail flow chart of an inspecting method in an embodiment of the present disclosure.

FIG. 5 is a detail flow chart of an inspecting method 500 in an embodiment of the present disclosure. The inspecting method 500 illustrates the steps to perform the inspecting method in reference with FIG. 3 at the same time. The inspecting method 500 includes the steps outlined below (The steps are not recited in the sequence in which the steps are performed. That is, unless the sequence of the steps is expressly indicated, the sequence of the steps is interchangeable, and all or part of the steps may be simultaneously, partially simultaneously, or sequentially performed).

In step 501, the mono-color image-retrieving module 10 is disposed above the inspection target with the optical axis O orienting toward the inspection target 2.

In step 502, the illuminating modules 12 are controlled to sequentially generate the illuminating lights 11 with different incident angles, e.g. the target regions A-E. For example, the control module 14 controls the illuminating modules 12 to sequentially generate the red color lights to illuminate the target areas A and B, the green color lights to illuminate the target area C and the blue color lights to illuminate the target areas D and E.

In step 503, the mono-color image-retrieving module 10 is controlled to sequentially retrieve the mono-color images 13 each in response to one incident angle of the illuminating lights 11. It is appreciated that in an embodiment, the mono-color image-retrieving module 10 retrieves the mono-color images 13 synchronously with the illumination of the illuminating lights 11.

In step 504, the control module 14 performs inspection by obtaining the profile 17 of the inspection target 2 according to the mono-color images 13 retrieved based on the illuminating lights 11 in the order of the different illumination angles.

Figure 6:
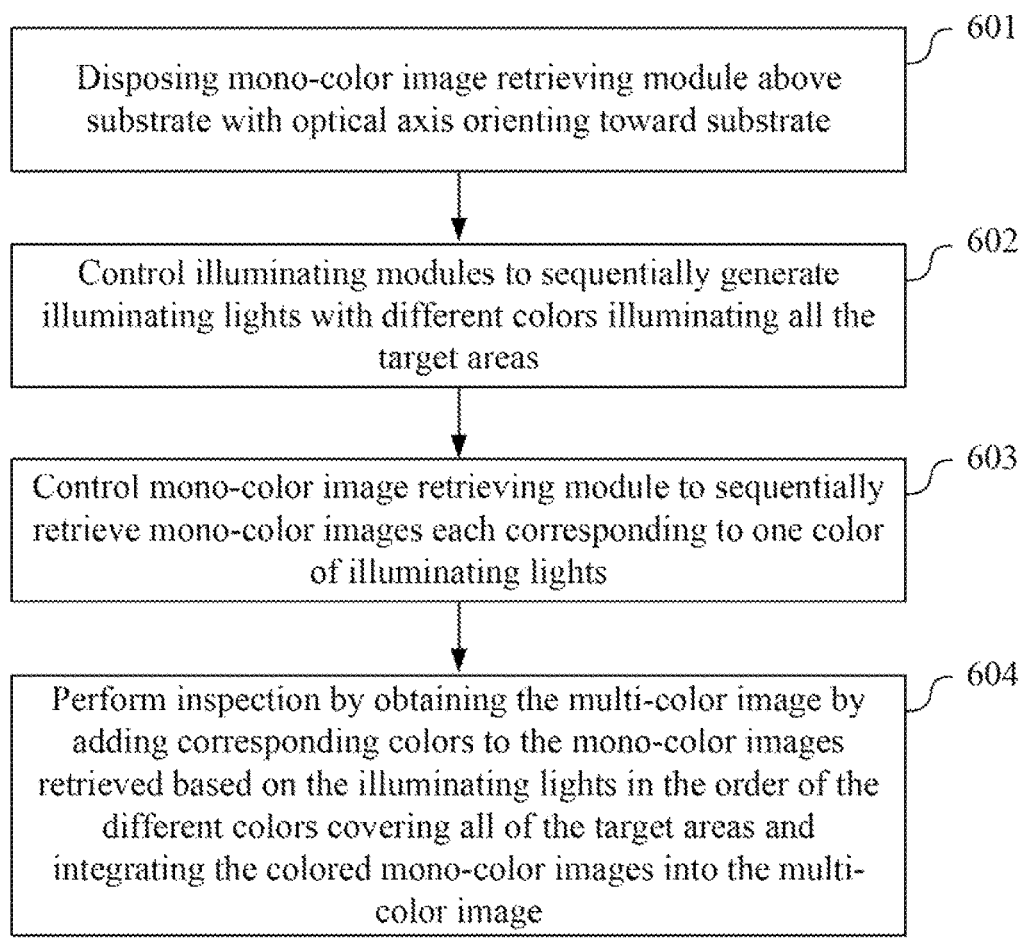
FIG. 6 is a detail flow chart of an inspecting method in an embodiment of the present disclosure.

FIG. 6 is a detail flow chart of an inspecting method 600 in an embodiment of the present disclosure. The inspecting method 600 illustrates the steps to perform the inspecting method in reference with FIG. 3 at the same time. The inspecting method 600 includes the steps outlined below (The steps are not recited in the sequence in which the steps are performed. That is, unless the sequence of the steps is expressly indicated, the sequence of the steps is interchangeable, and all or part of the steps may be simultaneously, partially simultaneously, or sequentially performed).

In step 601, the mono-color image-retrieving module 10 is disposed above the inspection target with the optical axis O orienting toward the inspection target 2.

In step 602, the illuminating modules 12 are controlled to sequentially generate the illuminating lights 11 with different colors illuminating all the target areas. For example, the control module 14 controls the illuminating modules 12 to sequentially generate the red color lights to illuminate all the target areas A-E, the green color lights to illuminate all the target areas A-E and the blue color lights to illuminate all the target areas A-E.

In step 603, the mono-color image-retrieving module 10 is controlled to sequentially retrieve the mono-color images 13 each in response to one color of the illuminating lights 11. It is appreciated that in an embodiment, the mono-color image-retrieving module 10 retrieves the mono-color images 13 synchronously with the illumination of the illuminating lights 11.

In step 604, the control module 14 performs the inspection of the inspection target 2 by obtaining the multi-color image 19 by adding corresponding colors to the mono-color images 13 retrieved based on the illuminating lights 11 in the order of the different colors covering all of the target areas and integrating the colored mono-color images into the multi-color image 19.

It is appreciated that the method of performing inspection by obtaining the profile described in FIG. 5, and the method of performing inspection by obtaining the multi-color image described in FIG. 6 can be performed either simultaneously or sequentially. When the methods in FIG. 5 and FIG. 6 are performed sequentially, either the method in FIG. 5 or FIG. 6 can be performed first while the other is performed subsequently.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fail within the scope of the following claims.

What is claimed is:
1. An inspecting device for inspecting an inspection target, comprising:
 a grayscale image-retrieving module disposed above the inspection target with an optical axis orienting toward the inspection target;

a plurality of illuminating modules each comprising a plurality of light-emitting elements of different colors around the optical axis such that each of a plurality of illumination angles between the optical axis and one of the illuminating modules is within a specified angular range with respect to one of a plurality target areas on the inspection target; and a control module electrically connected to the illuminating modules and the grayscale image-retrieving module to control the illuminating modules to sequentially generate a plurality of illuminating lights both in an order of different colors and different illumination angles to further control the grayscale image-retrieving module to sequentially retrieve a plurality of grayscale images each in response to one illumination of the illuminating lights;

wherein the control module performs an inspection of the inspection target based on the grayscale images.

2. The inspecting device of claim 1, wherein the control module controls the illuminating modules to sequentially generate the illuminating lights in the order of the different illumination angles each illuminating at least one part of the target areas to further control the grayscale image-retrieving module to sequentially retrieve the grayscale images accordingly.

3. The inspecting device of claim 2, wherein the inspection of the inspection target comprises obtaining a profile of the inspection target according to the grayscale images retrieved based on the illuminating lights in the order of the different illumination angles.

4. The inspecting device of claim 3, wherein the profile of the inspection target is obtained by performing trigonometric measurements based on information of the grayscale images by the control module.

5. The inspecting device of claim 1, wherein the control module controls the illuminating modules to sequentially generate the illuminating lights in the order of the different colors illuminating all the target areas to further control the grayscale image-retrieving module to sequentially retrieve the grayscale images accordingly.

6. The inspecting device of claim 5, wherein the inspection of the inspection target comprises obtaining a multi-color image by adding corresponding colors to the grayscale images retrieved based on the illuminating lights in the order of the different colors covering all of the target areas and integrating the colored grayscale images into the multi-color image.

7. The inspecting device of claim 1, wherein the light-emitting elements comprise a red light-emitting element, a green light-emitting element and a blue light-emitting element.

8. The inspecting device of claim 7, wherein the grayscale images at least comprises a first image corresponding to red color lights, a second image corresponding to green color lights and a third image corresponding to blue color lights.

9. An inspecting method for inspecting an inspection target used in an inspecting device, wherein the inspecting method comprises:

disposing a grayscale image-retrieving module above the inspection target with an optical axis orienting toward the inspection target;

controlling a plurality of illuminating modules to sequentially generate a plurality of illuminating lights both in an order of different colors and different illumination angles, wherein each of the illuminating modules comprises a plurality of light-emitting elements of different colors around the optical axis such that each of the illumination angles between the optical axis and one of the illuminating modules is within a specified angular range with respect to one of a plurality target areas on the inspection target;

controlling the grayscale image-retrieving module to sequentially retrieve a plurality of grayscale images each in response to one illumination of the illuminating lights; and performing an inspection of the inspection target based on the grayscale images.

10. The inspecting method of claim 9, further comprising:
controlling the illuminating modules to sequentially generate the illuminating lights in the order of the different illumination angles each illuminating at least one part of the target areas; and controlling the grayscale image-retrieving module to sequentially retrieve the grayscale images accordingly.

11. The inspecting method of claim 10, wherein the step of performing the inspection of the inspection target further comprises obtaining a profile of the inspection target according to the grayscale images retrieved based on the illuminating lights in the order of the different illumination angles.

12. The inspecting method of claim 11, further comprising obtaining the profile of the inspection target by performing trigonometric measurements based on information of the grayscale images.

13. The inspecting method of claim 9, further comprising:
controlling the illuminating modules to sequentially generate the illuminating lights in the order of the different colors illuminating all the target areas; and controlling the grayscale image-retrieving module to sequentially retrieve the grayscale images accordingly.

14. The inspecting method of claim 13, wherein the step of performing the inspection of the inspection target further comprises obtaining a multi-color image by adding corresponding colors to the grayscale images retrieved based on the illuminating lights in the order of the different colors and integrating the colored grayscale images into the multi-color image.

15. The inspecting method of claim 9, wherein the light-emitting elements comprise a red light-emitting element, a green light-emitting element and a blue light-emitting element.

16. The inspecting method of claim 15, wherein the grayscale images at least comprises a first image corresponding to red color lights, a second image corresponding to green color lights and a third image corresponding to blue color lights.

* * * * *